(12) United States Patent
Mosler et al.

(10) Patent No.: US 10,479,751 B2
(45) Date of Patent: Nov. 19, 2019

(54) PROCESS FOR PREPARING ACRYLIC ACID

(71) Applicant: EVONIK DEGUSSA GMBH, Essen (DE)

(72) Inventors: Jürgen Mosler, Marl (DE); Christian Psiorz, Ratingen (DE); Franz-Felix Kuppinger, Marl (DE); Raphael Schriewer, Laer (DE); Arnd Bruhns, Borgholzhausen (DE); Armin Rix, Marl (DE); Peter Kreis, Dortmund (DE); Ralf Meier, Dortmund (DE); James Edward Elder, Friendswood, TX (US)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/915,929

(22) PCT Filed: Aug. 11, 2014

(86) PCT No.: PCT/EP2014/067137
§ 371 (c)(1),
(2) Date: May 4, 2016

(87) PCT Pub. No.: WO2015/028293
PCT Pub. Date: Mar. 5, 2015

(65) Prior Publication Data
US 2016/0257637 A1    Sep. 8, 2016

(30) Foreign Application Priority Data
Sep. 2, 2013   (DE) .................. 10 2013 217 386

(51) Int. Cl.
| | | |
|---|---|---|
| C07C 51/48 | (2006.01) | |
| C07C 51/25 | (2006.01) | |
| B01J 19/30 | (2006.01) | |
| B01D 3/14 | (2006.01) | |
| B01L 3/16 | (2006.01) | |
| B01D 3/16 | (2006.01) | |
| B01D 3/00 | (2006.01) | |
| B01D 3/22 | (2006.01) | |
| B01J 10/00 | (2006.01) | |
| C07C 57/04 | (2006.01) | |

(52) U.S. Cl.
CPC ............ *C07C 51/252* (2013.01); *B01D 3/009* (2013.01); *B01D 3/143* (2013.01); *B01D 3/163* (2013.01); *B01D 3/22* (2013.01); *B01J 10/00* (2013.01); *B01J 19/30* (2013.01); *B01L 3/16* (2013.01); *C07C 51/48* (2013.01); *C07C 57/04* (2013.01); *B01J 2219/3325* (2013.01)

(58) Field of Classification Search
CPC ....... C07C 51/252; C07C 51/48; C07C 57/04; B01D 3/009; B01D 3/16; B01D 3/163; B01D 3/143; B01D 3/22; B01J 10/00; B01J 19/30; B01J 2219/3325
See application file for complete search history.

(56) References Cited

U.S. PATENT DOCUMENTS

| | | | |
|---|---|---|---|
| 4,408,079 A | | 10/1983 | Merger et al. |
| 4,496,770 A | | 1/1985 | Duembgen et al. |
| 4,774,929 A | * | 10/1988 | Milliman .................. F41A 3/58 124/76 |
| 4,873,368 A | | 10/1989 | Kadowaki et al. |
| 5,426,221 A | | 6/1995 | Willersinn |
| 5,969,178 A | * | 10/1999 | Okamoto ................ C07C 45/35 560/208 |
| 6,069,271 A | * | 5/2000 | Tanimoto ................. B01J 8/067 422/198 |
| 6,293,528 B1 | * | 9/2001 | Monkelbaan .......... B01D 3/008 261/108 |
| 6,448,439 B1 | | 9/2002 | Eck et al. |
| 7,189,872 B2 | | 3/2007 | Yada et al. |
| 7,294,741 B2 | * | 11/2007 | Bub ...................... C07C 51/252 562/545 |
| 7,557,245 B2 | | 7/2009 | Nordhoff et al. |
| 7,557,246 B2 | | 7/2009 | Nordhoff et al. |
| 7,939,597 B2 | | 5/2011 | Bub et al. |
| 8,178,717 B2 | | 5/2012 | Balduf et al. |
| 8,198,481 B2 | | 6/2012 | Kuppinger et al. |
| 8,258,429 B2 | | 9/2012 | Bub et al. |
| 8,293,941 B2 | | 10/2012 | Kuppinger et al. |
| 8,309,668 B2 | | 11/2012 | Balduf et al. |
| 8,362,299 B2 | | 1/2013 | Hengstermann et al. |
| 8,426,637 B2 | | 4/2013 | Koestner et al. |
| 8,445,617 B2 | | 5/2013 | Balduf et al. |

(Continued)

FOREIGN PATENT DOCUMENTS

| | | |
|---|---|---|
| DE | 3042468 A1 | 6/1981 |
| DE | 19740252 A1 | 3/1993 |

(Continued)

OTHER PUBLICATIONS

German language International Search Report dated Mar. 20, 2015 in PCT/EP2014/067137 (3 pages).

(Continued)

*Primary Examiner* — Jafar F Parsa
*Assistant Examiner* — Blaine G Doletski
(74) *Attorney, Agent, or Firm* — Bernard Lau; Jason S. Ngui; Linda S. Li

(57) ABSTRACT

The present invention provides an apparatus comprising a feed arranged below the middle of the apparatus, a quenching agent inlet arranged above the feed, an outlet arranged below the feed and a draw arranged above the quenching agent inlet, the apparatus having a region provided with one or more packing elements, wherein at least one means which ensures the formation of a liquid layer having a height of at least 1 cm is present between the quenching agent inlet and a packing element present between the quenching agent inlet and feed. The present invention also provides a process for preparing acrylic acid, which includes a step of oxidizing acrolein, wherein the reaction mixture obtained in this oxidation is contacted with water as quenching agent in an inventive apparatus, and a composition obtainable as bottom product in the process according to the invention, comprising acrylic acid and water.

16 Claims, 2 Drawing Sheets

(56) References Cited

U.S. PATENT DOCUMENTS

Figure 1:
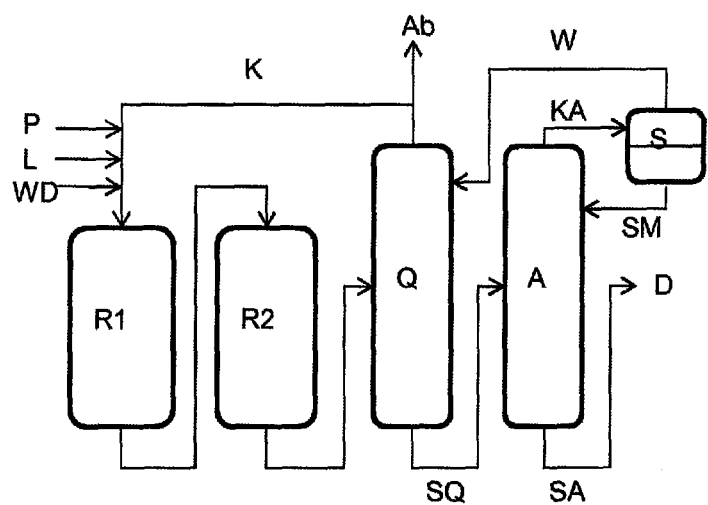

| | | |
|---|---|---|
| 8,481,784 B2 | 7/2013 | Kuppinger et al. |
| 8,524,945 B2 | 9/2013 | Kim et al. |
| 8,703,450 B2 | 4/2014 | Bub et al. |
| 8,841,481 B2 | 9/2014 | Zanthoff et al. |
| 8,895,683 B2 | 11/2014 | Kuppinger et al. |
| 9,156,768 B2 | 10/2015 | Meier et al. |
| 2001/0007043 A1 | 7/2001 | Machhammer et al. |
| 2003/0120112 A1* | 6/2003 | Hirao ............... B01D 53/1412 562/600 |
| 2007/0262022 A1 | 11/2007 | Mosler et al. |
| 2007/0274882 A1 | 11/2007 | Mosler et al. |
| 2007/0280866 A1 | 12/2007 | Balduf et al. |
| 2007/0295591 A1 | 12/2007 | Mosler |
| 2008/0183014 A1* | 7/2008 | Diefenbacher ......... C07C 51/44 562/600 |
| 2008/0197086 A1 | 8/2008 | Mosler |
| 2009/0068440 A1 | 3/2009 | Bub et al. |
| 2009/0134357 A1 | 5/2009 | Bub et al. |
| 2010/0144931 A1* | 6/2010 | Balduf .................. C07C 41/06 524/27 |
| 2014/0180234 A1 | 6/2014 | Bub et al. |
| 2015/0315115 A1 | 11/2015 | Kuppinger et al. |

FOREIGN PATENT DOCUMENTS

| | | |
|---|---|---|
| DE | 4308087 A1 | 9/1994 |
| DE | 102010028781 A1 | 11/2011 |
| EP | 0058927 A1 | 9/1982 |
| EP | 0092097 A1 | 10/1983 |
| EP | 0608838 A2 | 8/1984 |
| EP | 0982289 A2 | 3/2000 |
| EP | 1319648 A1 | 6/2003 |
| WO | 2006136336 A2 | 12/2006 |
| WO | 2007003353 A2 | 1/2007 |
| WO | 2010063529 A1 | 6/2010 |
| WO | 2012076505 A1 | 6/2012 |
| WO | 2015028293 A1 | 3/2015 |

OTHER PUBLICATIONS

German language Written Opinion dated Mar. 20, 2015 in PCT/EP2014/067137 (6 pages).

International Search Report dated Mar. 20, 2015 in PCT/EP2014/067137 (2 pages).

* cited by examiner

PROCESS FOR PREPARING ACRYLIC ACID

This application is a national stage application under 35 U.S.C. § 371 of International Application No. PCT/EP2014/067137 filed 11 Aug. 2014, which claims priority to German Application No. DE 10 2013 217 386.5 filed 2 Sep. 2013, the disclosures of which are expressly incorporated herein by reference.

FIELD

The present invention relates to an apparatus comprising a feed arranged below the middle of the apparatus, a quenching agent inlet arranged above the feed, an outlet arranged below the feed and a draw arranged above the quenching agent inlet, the apparatus having, between the quenching agent inlet and the feed, a region provided with one or more packing elements, which is characterized in that at least one means which ensures the formation of a liquid layer having a height of at least 1 cm is present between the quenching agent inlet and a packing element present between the quenching agent inlet and feed. The present invention also provides a process for preparing acrylic acid, which includes a step of oxidizing acrolein, wherein the reaction mixture obtained in this oxidation is contacted with water as quenching agent in an inventive apparatus, and a composition obtainable as bottom product in the process according to the invention, comprising acrylic acid and water.

BACKGROUND

Acrylic acid (prop-2-enoic acid) is a synthesis unit for the production of superabsorbents used principally in hygiene products, and a raw material for acrylate chemistry in its entirety. Acrylic acid is obtained on the industrial scale by catalytic vapour phase reaction of propene with oxygen. This gives rise not only to the desired acrylic acid, but also to undesired accompanying products which present difficulties in the further processing of the acrylic acid. These accompanying products are essentially acetic acid, aldehydes, dialdehydes, dicarboxylic acids and water. An important step in the preparation of acrylic acid (AA) is accordingly to purify the acrylic acid-containing composition originating from the vapour phase reaction to free it of the unwanted accompanying products, such that what remains is pure acrylic acid. The present invention addresses one aspect of this purification.

Acrylic acid is typically prepared by conventional chemical means via the oxidation of propene to acrolein and subsequent further oxidation to acrylic acid. EP 1319648 A1 discloses a process of this kind, in which acrylic acid (AA) is prepared by catalytic vapour phase oxidation of propylene in two steps. The process for preparing AA by the two-stage (the first catalytic oxidation reaction stage for the conversion of propylene principally to acrolein, and the second catalytic oxidation reaction stage for the conversion of acrolein to AA) catalytic vapour phase oxidation of propylene using molecular oxygen is already known and has been conducted on the industrial scale for many decades. For many reasons (inflammability limits for the propylene/air mixture and high heat of reaction), it is necessary to dilute the reaction gases with inert gases (for example water vapour, $N_2$, $CO_2$). A typical process for industrial preparation takes the following form: A mixture of propylene, air and steam is fed to a first oxidation reactor and the propylene is converted in the first step principally to acrolein and in small amounts to AA. The product is fed to a second oxidation reactor without separation. Fresh air and steam can, if required for the downstream oxidation reaction in the second oxidation step, be fed in at the inlet of the second oxidation reactor.

For the separation of gaseous AA from the steam in the output, which is at about 180° C., from the oxidation reactors, two separating processes are used: 1. Absorption of the gaseous AA in a high-boiling, hydrophobic, aromatic solvent at temperatures at which the process water remains in the process waste air gas, which leaves an absorption tower at the top (see, for example, DE 43 08 087 BASF, 15.09.94). 2. Absorption of AA in water with simultaneous quenching to low temperatures in a quench tower/collector in such a way that virtually all the process water evaporated condenses in the 180° C. output from the second reactor (see, for example, DE 30 42 468/Mitsubishi Chem. Corp. (MCC), 11.11.80). While the AA and high-boiling products are separated in many distillation steps in the first procedure, the water in the aqueous AA is removed in a subsequent azeotropic distillation after the quenching in the second procedure, in order to obtain a crude AA from which AA can be prepared with high purity for the preparation of AA copolymers or various AA esters.

In the second procedure, the handling of the process water, which consists of the water formed in the oxidation and the water for the dilution, which is required to be outside the inflammability limit, has a considerable influence on the economic viability of the process.

If the AA-containing product gas which is obtained at the outlet of the second oxidation reactor is introduced into the quench tower in order to obtain AA as an aqueous solution, the resulting process waste air gas containing unreacted propylene and other low-boiling organic materials leaves the quench tower at the top and has to be treated, for example, in an incineration furnace, such that no or virtually no organic compounds are emitted into the air (a flow process with one pass).

It is also possible that a portion of the process waste air gas is recycled and added to the propylene/air/steam stream at the inlet of the first reaction stage (cycle gas flow process), which is an entirely customary procedure particularly in the case that the process is operated with partial conversion of the propylene.

DE 10 2010 028 781 A1 describes the further separation of a mixture including aqueous acrylic acid obtained in a quench tower with the aid of a distillation column having a side draw.

U.S. Pat. No. 7,189,872 describes a process for preparing acrylic acid, in which a quench tower is used in order to separate acrylic acid from the gaseous product mixture. This aqueous mixture is subsequently separated by means of azeotropic distillation into a gaseous phase including water, and a liquid phase including acrylic acid.

In the acrylic acid preparation by oxidation of propene with atmospheric oxygen in low concentrations, secondary components are also formed, for example phthalic acid, terephthalic acid or isophthalic acid. These substances are high boiler compounds and are only sparingly soluble in water.

In the case of use of a quench tower for processing of the gaseous product mixture from the last oxidation reactor, the secondary components mentioned are obtained in the bottoms with the aqueous AA. The concentration of the secondary components (sum total of phthalic acid, terephthalic acid or isophthalic acid) is 0.024 to 0.030% by weight, based on the composition obtained in the quench tower bottoms.

The quench tower is frequently designed such that it can cool and condense the gaseous reaction mixture, but can also minimize the loss of acrylic acid in the tower tops. The quench tower is therefore typically equipped with distillation trays, for example bubble-cap trays or tunnel-cap or Thormann trays. Valve trays are also used.

If the throughput is to be increased significantly by means of such a quench tower, or the tops loss of the target product is to be reduced, it is frequently customary in the case of distillation trays to replace the trays with packing elements, especially structured packing elements.

It has been found here, however, that only a portion of the high boiler compounds is now discharged in the quench tower bottoms, and the other portion gets into the top of the column as an aerosol or desublimate, and leads to blockages therein and possibly in downstream apparatuses, such that the plant has to be shut down after only a short run time in order to conduct cleaning operations. In the column bottoms, the abovementioned secondary components are detected only in a concentration of <0.02% by weight based on the composition in the quench tower bottoms.

SUMMARY

The problem addressed by the present invention was therefore that of improving the run time of the quench tower again without reducing the throughput through the quench tower or increasing the tops loss of the target product.

It has been found that, surprisingly, this problem can be solved by providing at least one means which ensures the formation of a liquid layer having a height of at least 1 cm in the quench tower between inlet and a packing element present between quenching agent inlet and inlet.

The present invention therefore provides an apparatus comprising a feed arranged below the middle of the apparatus, a quenching agent inlet arranged above the feed, an outlet arranged below the feed and a draw arranged above the quenching agent inlet, the apparatus having, between the quenching agent inlet and the feed, a region provided with one or more packing elements, characterized in that at least one means which ensures the formation of a liquid layer having a height of at least 1 cm is present between the quenching agent inlet and a packing element present between quenching agent inlet and feed.

DETAILED DESCRIPTION

The present invention likewise provides a process for preparing acrylic acid, which includes a step of oxidizing acrolein, wherein the reaction mixture obtained in this oxidation is contacted with water as quenching agent in an inventive apparatus. Water used may, for example, be demineralized water or process water, which may possibly contain acetic acid, propionic acid and small amounts of acrylic acid, from a downstream water removal column.

The present invention also provides a composition obtainable as bottom product in the process according to the invention, comprising predominantly acrylic acid and water ("predominantly" means here that the sum total of acrylic acid and water is more than 50% by weight, based on the product mixture).

The process according to the invention has the advantage that, given approximately equal throughput and without an increase in the tops losses of target product in the quench tower, the run time (service life) is increased.

A further advantage of the process according to the invention is that the entrainment or discharge of dicarboxylic acids together with the top stream is avoided or at least reduced, such that the dicarboxylic acids do not disrupt the further workup of the top product.

A further advantage of the process according to the invention is that the use of a sieve tray can avoid blockages, as occur in the case of use of other trays, for example in the case of use of tunnel trays, which in turn results in a longer run time or longer maintenance intervals. The necessary interruptions to operation are thus distinctly reduced through the utilization of the process according to the invention.

The subject-matter of the invention is described hereinafter by way of example, without any intention of limiting the invention to these illustrative embodiments. When ranges, general formulae or compound classes are specified hereinafter, these shall include not just the corresponding ranges or groups of compounds that are explicitly mentioned but also all sub-ranges and sub-groups of compounds which can be obtained by removing individual values (ranges) or compounds. When documents are cited in the context of the present description, the contents thereof, particularly with regard to the subject-matter that forms the context in which the document has been cited, are considered in their entirety to form part of the disclosure-content of the present invention. Unless stated otherwise, percentages are figures in percent by weight. If mean values are reported hereinafter, the values in question are weight averages, unless stated otherwise. When parameters which have been determined by measurement are reported hereinafter, they have been determined at a temperature of 25° C. and a pressure of 101 325 mbar, unless stated otherwise.

It is a feature of the inventive apparatus comprising a feed arranged below the middle of the apparatus, a quenching agent inlet arranged above the feed, an outlet arranged below the feed and a draw arranged above the quenching agent inlet, the apparatus having, between the quenching agent inlet and the feed, a region provided with one or more packing elements, that at least one means which ensures the formation of a liquid layer having a height of at least 1 cm, preferably having a height of 2 to 10 cm, more preferably having a height of 3 to 5 cm, is present between the quenching agent inlet and a packing element present between the quenching agent inlet and feed, the liquid layer being arranged in the apparatus such that gaseous substances which pass through the feed into the apparatus have to pass through the liquid layer in order to get into the top of the apparatus, for which reason the liquid layer is also referred to as a froth layer.

Suitable means may, for example, be sieve trays, ripple trays, bubble-cap trays, tunnel-cap trays or Thormann trays. In the case of configuration of the means in such a way that the gases flowing upward have contact with the means over a prolonged period before passing through the liquid layer, as is the case, for example, in bubble-cap trays, tunnel-cap trays or Thormann trays, there may be deposits of diacids on the surfaces of these means. It is therefore particularly advantageous to use, as means, those where the gases flowing upward pass through the liquid layer without prolonged contact with the means, as is the case, for example, in the case of ripple trays or sieve trays, for which reason these are particularly preferred as means.

Preferably, in the inventive apparatus, from 1 to 5, preferably 2 or 3, more preferably 3, of the means are present between the quenching agent inlet and a packing element present between the quenching agent inlet and feed.

Packing element(s) present in the inventive apparatus may be all kinds of suitable packing elements. Preferably, the packing element(s) are structured packing elements or fabric packing elements, preferably structured packing elements. Suitable packing elements are sold, inter alia, by Sulzer under the Mellapak trade names, by Raschig under the Super-Pak trade name, by Koch-Glitsch under the Flexi-Pak trade name, and by Montz under the Montz-Pak trade names.

The packing element(s) in the inventive apparatus preferably have a packing element height which amounts to 40 to 85%, preferably 45 to less than 55%, of the internal height of the apparatus. If more than one packing element is present in the inventive apparatus, the height of the packing element is calculated from the sum of the heights of the individual packing elements. The internal height of the apparatus is found by determining the distance from the highest point in the top of the apparatus to the lowest point in the bottom of the apparatus.

It may be advantageous when a distributor present between the lowermost means above the packing element and the uppermost packing element distributes the liquid phase flowing downward from the lowermost means with maximum homogeneity over the packing element. If such a distributor is present, it has also been found to be advantageous when a collector arranged between the lowermost means and distributor collects the liquid phase flowing downward from the lowermost means and feeds it to the distributor.

The inventive apparatus can be used in all processes in which a gaseous reaction mixture is contacted with a quenching agent, especially a liquid quenching agent. Preferably, the inventive apparatus is used in a process for preparing acrylic acid, preferably in the process according to the invention described hereinafter.

It is a feature of the process according to the invention for preparing acrylic acid, including a step of oxidizing acrolein, that the reaction mixture obtained in this oxidation is contacted with water as quenching agent in an inventive apparatus as described above. The quenching agent used may be water, as described above.

The reaction mixture used may be any mixture including acrylic acid, which is preferably in gaseous form. Suitable mixtures can be obtained, for example, by processes for preparing acrylic acid as described in DE 19740252, EP 0092097, EP 0058927 or EP 0608838. In relation to the preparation of acrylic acid, reference is made explicitly to the details given in the documents cited.

The ratio of the volume flow rates of quenching agent which is fed to the apparatus to reaction mixture which is fed to the apparatus is preferably from 1:2 to 1:20, more preferably from 1:5 to 1:10 and especially preferably from 1:7 to 1:8.

The apparatus is fed preferably with from 210 kg to 380 kg, more preferably with from 230 kg to 260 kg, of reaction mixture per m$^3$ of apparatus volume per hour. The apparatus volume is the volume of the apparatus minus the volume of the internals. The apparatus volume can be determined by filling the apparatus with a liquid.

The temperature of liquid phase on the means is preferably from 50° C. to 100° C., more preferably from 60° C. to 90° C. and especially preferably from 70° C. to 80° C. The temperature can be adjusted by varying the volume flow rates and via the thermal energy fed to the apparatus.

In the process according to the invention, the apparatus is preferably operated in such a way that the pressure differential between the pressure measured at the top of the apparatus and the pressure measured in the gas space of the liquid phase in the bottom of the apparatus is from 10 mbar to 60 mbar, preferably from 30 mbar to 40 mbar.

By means of the process according to the invention, compositions (product mixtures) comprising predominantly acrylic acid and water are obtainable. Preferably, the composition is obtained as bottom product (of the apparatus used in accordance with the invention) in the process according to the invention. The inventive composition preferably contains acrylic acid, water, phthalic acid, terephthalic acid and isophthalic acid, the proportion of the sum total of phthalic acid, terephthalic acid and isophthalic acid preferably being greater than 0.05% by weight, more preferably from 0.05 to 1% by weight and especially preferably from 0.052 to 0.075% by weight, based on the composition. The sum total of water and acrylic acid is preferably greater than 90% by weight, more preferably greater than 95% by weight, based on the composition. The proportion of acrylic acid in the composition is preferably from 50 to 65% by weight, preferably 53 to 62% by weight, based on the composition. The preferred proportion of water is calculated correspondingly from the values reported for the sum total of acrylic acid and water. Particularly preferred inventive compositions have a proportion of the sum total of phthalic acid, terephthalic acid and isophthalic acid of preferably greater than 0.05% by weight, more preferably from 0.05 to 1% by weight and especially preferably from 0.052 to 0.075% by weight, based on the composition, and a proportion of the sum total of water and acrylic acid of preferably greater than 90% by weight, more preferably greater than 95% by weight, based on the composition. As further components, the inventive compositions may include acetic acid, maleic acid, hydroquinone, diacrylic acid, formaldehyde and propionic acid. Particularly preferred inventive compositions include from 2 to 3% by weight of acetic acid, from 0.1 to 0.3% by weight of maleic acid, from 0.03 to 0.1% by weight of hydroquinone, from 0.15 to 0.25% by weight of diacrylic acid, from 0.5 to 1.25% by weight of formaldehyde and from 0.01 to 0.05% by weight of propionic acid, based in each case on the composition.

The compositions (product mixtures) obtained in accordance with the invention can be sent to a further workup. More particularly, the composition can be worked up as described in DE 10 2010 028 781 A1 or U.S. Pat. No. 7,189,872, to which explicit reference is made.

Figure 2:
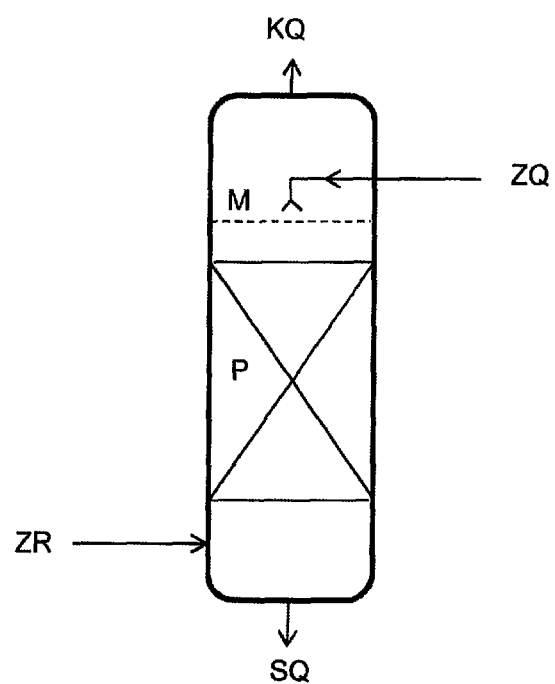

The present invention is illustrated in detail by the figures, FIG. 1 and FIG. 2, without any intention that the invention be restricted to these embodiments.

FIG. 1 shows, in schematic form (customary apparatuses, for example slide vanes, taps, pumps or heat exchangers are not shown for the sake of better clarity), a plant for preparation of acrylic acid from propene. Propene P, steam (WD) and air (L) are passed into the first oxidation reactor R1. The reaction product comprising acrolein is passed into a second oxidation reactor R2 in which the acrolein is oxidized to acrylic acid. The gaseous reaction product from reactor R2 is run into the side of the quench tower Q in which water is introduced from the top. The gaseous top product from the quench tower can be sent partly as offgas to a further workup or disposal operation, and partly returned to the reactor R1 as cycle gas. The bottom product of the quench tower SQ is transferred into the side of the distillation column A, in which an azeotroping agent/azeotropic distillation is conducted. The top product KA is condensed and transferred into a separator S in which the top product is separated into an aqueous phase and a phase including the azeotroping agent. The azeotroping agent is recycled into the distillation column A above the feed of the bottom product SQ. The aqueous phase W obtained in the separator S is recycled into the quench tower above the feed of the reaction product from the reactor R2. The bottom product SA of column A can be sent to a further processing operation D.

FIG. 2 shows, in schematic form, one setup of an inventive apparatus (of a quench tower): The apparatus has been provided with a feed for the reaction mixture ZR, an inlet for the quenching agent ZQ, an outlet in the bottom SQ and a draw for the top product KQ. Provided therein is a packing element P, above which is arranged a means M which assures the formation of a liquid layer having a height of at least 1 cm.

The examples adduced below illustrate the present invention by way of example, without any intention of restricting the invention, the scope of application of which is apparent from the entirety of the description and the claims, to the embodiments specified in the examples.

EXAMPLES

Measurement Method:

The proportion of phthalic acid, isophthalic acid and terephthalic acid in the bottom product of the apparatus was determined by means of GC-MS as dimethyl esters. For this purpose, the samples were first admixed with diazomethane for esterification. The samples thus prepared were sent to the GC-MS (described hereinafter for terephthalic acid, to be conducted in an equivalent manner for phthalic acid/isophthalic acid). The following instruments were used: liquid sampler, PAL injector 80; Agilent GC 7890 gas chromatograph and Agilent MSD 5975 mass spectrometer.

The measurements were effected with the following parameters:

Capillary column: 30 m DB-5; internal diameter 0.25 mm; film 0.25 µm
Carrier gas: helium
Column flow rate: approx. 1 ml/min
Injector: 300° C. (0.5 min splitless, then 50 ml/min)
Oven temperature: 60° C.-8° C./min-250° C. (15 min)
Injection volume: 1.0 µl
Detector (MSD): single ion monitoring (SIM)
Group 1 (6 min to 12 min): (91.0; 100 msec), (119.0; 100 msec), (150; 100 msec)
Group 2 (from 12 min): (163.0; 100 msec), (194.0; 100 msec)
The reagents used were:
diazomethane derivatizing agent
methanol
terephthalic acid dopant solution (concentration=1 mg/ml, dissolved in methanol)
Sample Preparation
Derivatization of the Sample 25 mg of sample were dissolved in 1 ml of methanol and derivatized with diazomethane. The reaction mixture is then concentrated down to 1.5 ml in a water bath. The overall solution is transferred into a 2 ml standard flask and made up to the mark with methanol.

Derivatization of the terephthalic acid-doped Sample 25 mg of sample were dissolved in 1 ml of methanol, 10 µl of the terephthalic acid dopant solution were added, and then derivatization was effected with diazomethane. The reaction mixture is then concentrated down to 1.5 ml in a water bath. The overall solution is transferred into a 2 ml standard flask and made up to the mark with methanol.

Evaluation

Terephthalic acid was detected in the GC-MS analysis as dimethyl terephthalate. The dimethyl terephthalate peak is identified on the basis of the run time and on the basis of the ratio of the two ions measured, m/z 163 and m/z 194 (two characteristic ions for dimethyl terephthalate). The mass content of terephthalic acid in the sample is calculated using the measured values from the measurement of the undoped sample and from the doped sample:

$$wT = \frac{(m, Tdot.)}{\left(\left(\frac{(A(T, dot.) \times E)}{E(dot.) \times A(T)}\right) - 1\right) \times E(dot.)}$$

w(T): proportion by mass of terephthalic acid in the sample (in mg/g)
m(T, dot.): mass of terephthalic acid dopant in the doped sample (in µg)
A(T, dot.): peak area of the dimethyl terephthalate in the doped sample
E(dot.): starting sample weight in the doped measurement (in mg)
A(T): peak area of dimethyl terephthalate in the undoped sample
E: starting sample weight in the undoped measurement (in mg)

Apparatus:

The apparatus used was a quench tower having a capacity of 300 m³ and an internal height of 35.05 m. Installed in the apparatus were 19 packing elements of the Montz-Pak B1-125.60 type at an internal height of 3.96 to 8.102 m, 42 packing elements of the Montz-Pak B1-250 type at an internal height of 10.975 to 19.585 m, and 32 packing elements of the Montz-Pak B1-250 type at an internal height of 21.97 to 28.53 m. The inlet for the quenching agent was installed at an internal height of 32.598 m; the reaction mixture was fed in at an internal height of 5.048 m. In the comparative example, a quench tower of this kind which did not have any sieve trays was used. The inventive quench tower had, at an internal height of 28.3 m, a sieve tray with which a liquid layer of 3 cm was achievable. The size of the uppermost packing element was reduced, such that it extended from an internal height of 21.97 to 27.3 m. The quench tower additionally had liquid distributors, gas distributors, collectors and standard support grids for the packing elements. A top draw was present at the top of the quench tower, and a bottoms outlet in the bottom of the column.

Comparative Example 1: Acrylic Acid Preparation Without the Use of an Inventive Quench Tower In a plant as shown schematically in FIG. 1 for preparation of acrylic acid, a reaction mixture stream which included 6.24% by volume of acrylic acid and a content of the sum total of phthalic acid, isophthalic acid and terephthalic acid of 0.0144% by weight was introduced into the quench tower at 71 141 kg/h. Via the inlet for the quenching agent, 8200 kg/h of water were fed in. Via the bottoms outlet, a product stream of 18 252 kg/h was withdrawn. Via the top draw, an offgas stream of 61 089 kg/h was withdrawn. The bottom temperature was set to 79.1° C. and the top temperature to 71.6° C. After three hours of continuous operation, the samples were taken from the bottoms. The results of the analysis are reported in Table 1.

The plant had to be shut down after 33 days of operation, since the pressure drop between the reaction mixture feed and top draw had risen by more than 50% compared to the value on startup of the plant.

Example 1: Preparation of Acrylic Acid Using an Inventive Quench Tower

In a plant as described in the comparative example, instead of the quench tower described therein, an inventive quench tower which had a sieve tray was used. After three hours of continuous operation, the samples were taken from the bottoms. The results of the analysis are again reported in Table 1.

In contrast to the comparative experiment, it was still possible to conduct the preparation of acrylic acid without any problem even after 2 months. In a standard inspection of the plant after 3 months, absolutely no deposits attributable to phthalic acid, terephthalic acid or isophthalic acid or conversion products thereof were observed in the top of the quench tower.

Comparative Example 2: Quench Tower Without Packing Elements and Without Sieve Trays Comparative example 1 was repeated, except using a quench tower which, rather than the B1-250 packing elements, had 25 Thormann trays and, below that, instead of the B1-125.60 packing elements, 7 segmented cascade trays.

TABLE 1

Content of diacids in the bottom product based on the overall composition of the bottom product

| | Sum total of phthalic acid and terephthalic acid | Isophthalic acid | Reaction mixture stream throughput |
|---|---|---|---|
| Comparative example 1 | 0.016% by weight | 0.026% by weight | 71 141 kg/h |
| Example 1 | 0.030% by weight | 0.026% by weight | 71 141 kg/h |
| Comparative example 2 | 0.028% by weight | 0.026% by weight | 51 100 kg/h |

As can be inferred from Table 1, the bottom product which was obtained in an inventive apparatus (Example 1) has a proportion of phthalic acid and terephthalic acid well above the proportion which was determined for Comparative Example 1. Using a quench tower without packing elements (Comparative Example 2), it is possible to achieve similar proportions of phthalic acid and terephthalic acid to those reported for the inventive apparatus, but only with acceptance of a distinct decrease in throughput.

The invention claimed is:

1. An apparatus consisting essentially of
a feed containing a reaction mixture arranged below the middle of the apparatus,
a quenching agent inlet arranged above the feed,
an outlet arranged below the feed and
a draw arranged above the quenching agent inlet,
the apparatus having, between the quenching agent inlet and the feed containing the reaction mixture, a region provided with one or more packing elements, wherein 2 or 3 sieve trays or ripple trays which ensure the formation of a liquid layer having a height of at least 1 cm is present between the quenching agent inlet and a packing element present between the quenching agent inlet and feed containing the reaction mixture, the liquid layer being arranged in the apparatus such that gaseous substances which pass through the feed containing the reaction mixture into the apparatus have to pass through the liquid layer in order to get into the top of the apparatus.

2. The apparatus according to claim 1, wherein the liquid layer has a height of 2 to 10 cm.

3. The apparatus according to claim 1 wherein the packing element is a structured packing element or a fabric packing element.

4. The apparatus according to claim 1, wherein the packing element has a height of 50 to 85% of the internal height of the apparatus.

5. The apparatus according to claim 1, wherein a distributor present between a lowermost sieve trays or ripple trays and the uppermost packing element distributes the liquid phase flowing downward from the lowermost sieve trays or ripple trays over the packing element.

6. The apparatus according to claim 5, wherein a collector arranged between the lowermost sieve trays or ripple trays and distributor collects the liquid phase flowing downward from the lowermost sieve trays or ripple trays and feeds liquid phase to the distributor.

7. A process for preparing acrylic acid, including a step of oxidizing acrolein, wherein the reaction mixture obtained in this oxidation is contacted with water as quenching agent in an apparatus consisting essentially of
a feed containing a reaction mixture arranged below the middle of the apparatus,
a quenching agent inlet arranged above the feed,
an outlet arranged below the feed and
a draw arranged above the quenching agent inlet,
the apparatus having, between the quenching agent inlet and the feed containing the reaction mixture, a region provided with one or more packing elements, wherein 2 or 3 sieve trays or ripple trays which ensure the formation of a liquid layer having a height of at least 1 cm is present between the quenching agent inlet and a packing element present between the quenching agent inlet and feed containing the reaction mixture, the liquid layer being arranged in the apparatus such that gaseous substances which pass through the feed containing the reaction mixture into the apparatus have to pass through the liquid layer in order to get into the top of the apparatus.

8. The process according to claim 7, wherein the ratio of the volume flow rates of the quenching agent which is fed to the apparatus and the reaction mixture which is fed to the apparatus is from 1:2 to 1:20.

9. The process according to claim 7, wherein the temperature of the liquid phase on the sieve trays or ripple trays is from 50° C. to 100° C.

10. The process according to claim 7, wherein the pressure differential between the pressure measured at the top of the apparatus and the pressure measured in the gas space of the liquid phase in the bottom of the apparatus is from 10 mbar to 60 mbar.

11. The process according to claim 7 wherein the apparatus is fed with 210 to 380 kg of reaction mixture per hour per $m^3$ of apparatus volume.

12. The apparatus according to claim 2, wherein the liquid has a height of 3 to 8 cm.

13. The apparatus according to claim 3, wherein the packing element is a structured packing.

14. The process according to claim 8, wherein the ratio of the volume flow rates of the quenching agent which is fed to the apparatus and the reaction mixture which is fed to the apparatus is from 1:5 to 1:10.

15. The process according to claim 9, wherein the temperature of the liquid phase on the sieve trays or ripple trays is from 70° C. to 80° C.

16. The process according to claim 10, wherein the apparatus is operated in such a way that the pressure differential between the pressure measured at the top of the apparatus and the pressure measured in the gas space of the liquid phase in the bottom of the apparatus is from 30 mbar to 40 mbar.

\* \* \* \* \*